United States Patent
Speckbacher et al.

(10) Patent No.: US 7,473,281 B2
(45) Date of Patent: Jan. 6, 2009

(54) COLORANTS CONTAINING CATIONIC INDAZOLINE THIAZOLAZO DYE

(75) Inventors: Markus Speckbacher, Flamatt (DE); Hans-Jürgen Braun, Ueberstorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/728,855

(22) Filed: Mar. 27, 2007

(65) Prior Publication Data

US 2008/0034510 A1    Feb. 14, 2008

Related U.S. Application Data

(63) Continuation of application No. PCT/EP2005/010319, filed on Sep. 23, 2005.

(30) Foreign Application Priority Data

Oct. 12, 2004    (DE) .................. 10 2004 049 600

(51) Int. Cl.
*A61Q 5/10* (2006.01)
*C07D 277/00* (2006.01)

(52) U.S. Cl. .................. 8/405; 8/406; 8/407; 8/409; 8/437; 8/570; 8/571; 548/146; 548/300.1

(58) Field of Classification Search .................. 8/405, 8/406, 407, 409, 437, 570, 571; 548/146, 548/300.1
See application file for complete search history.

(56) References Cited

OTHER PUBLICATIONS

Tarabasanu-mihaila et al. (Heterocyclic derivatives with thiazolic rings) 1973, 18 (5), 889-98.*
STIC Search Report dated Mar. 31, 2008.*
Tarabasanu-Mihaila, C. et al., *Revue Roumaine de Chimie*, 1973, 18(5), 889-898.

* cited by examiner

*Primary Examiner*—Eisa B Elhilo
(74) *Attorney, Agent, or Firm*—Melissa Krasovec; Marianne Dressman; Idris N. McKelvey

(57) ABSTRACT

Colorant for keratin fibers containing cationic indazoline thiazolazo dyes of the general formula (I).

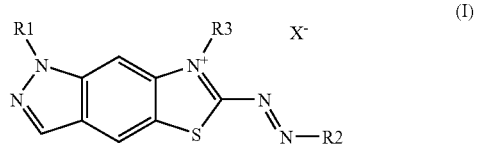

9 Claims, No Drawings

COLORANTS CONTAINING CATIONIC INDAZOLINE THIAZOLAZO DYE

FIELD OF THE INVENTION

The present invention relates to colorants containing cationic indazoline thiazolazo dye for keratin fibers such as hair, wool, or fur.

BACKGROUND OF THE INVENTION

Oxidative dyes resulting from the oxidative coupling of one or more developer components with one or more coupler components or direct-penetrating dyes are used to color keratin-containing fibers. If necessary, oxidation-stable, direct-penetrating dyes can be added to obtain particular color effects. Direct-penetrating dyes are incorporated into suitable carrier mixtures to then be applied to the fiber. This process, generally known as tinting, is simple to use, particularly mild, and distinguishes itself by causing little damage to the keratin fiber, because no ammonia or peroxide is added. However, the dyes used in this process must meet a few requirements. They must be toxicologically and dermatologically harmless and enable obtainment of colors in the desired intensity and brilliance. Furthermore, the colors obtained must have good light resistance and resistance to shampoo or hair care products, as well as good friction resistance.

Normally, a combination of different non-oxidative dyes is needed for a direct-penetrating, non-oxidative colorant for keratin fibers in order to obtain certain nuances. Because there is a limited selection of dyes that sufficiently meet the requirements mentioned, there continues to be a great need for these types of dyes.

An additional, very interesting application for direct-penetrating dyes is found in their use in agents for simultaneously lightening and coloring. With these colorants, which can contain a greater amount of oxidizing agents, even more extensive requirements are placed on the dyes used, particularly with respect to sufficient resistance to the oxidizing agents used.

Up to now, there have only been a few dyes that meet the prerequisites mentioned and simultaneously provide satisfactory coloring results. Thus, the object of the present invention is to provide direct-penetrating dyes to color keratin fibers, particularly human hair, that will meet these requirements.

Surprisingly, it has now been found that cationic indazoline thiazolazo dyes of the general formula (I) can be very easily applied to keratin fibers as direct-penetrating dyes in color mixtures without the addition of an oxidizing agent. Because these dyes are stable with regard to oxidizing agents, they can also be used in lightening colorants containing oxidizing agents, for example, peroxides or persulfates.

The object of the present invention is thus (a) An agent for non-oxidative coloring of keratin fibers, particularly human hair;

(b) An agent for simultaneously lightening and coloring keratin fibers that contains an oxidizing agent in addition to the dye of the formula (I); and (c) An oxidative colorant for keratin fibers based on at least one oxidative dye precursor, wherein the agents (a), (b), and (c) are characterized in that they each contain at least one cationic indazoline thiazolazo dye of the general formula (I);

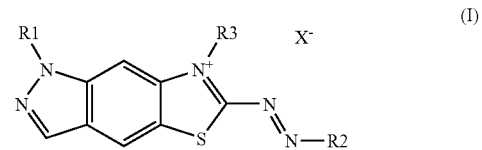

wherein

R1 stands for a hydrogen atom, a $C_1$-$C_6$-alkyl amino group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, and a $C_1$-$C_6$-alkyl sulfonic acid ester group;

R2 represents a group of the general formulas (II), (III), or (IV);

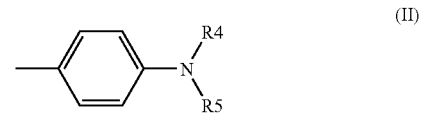

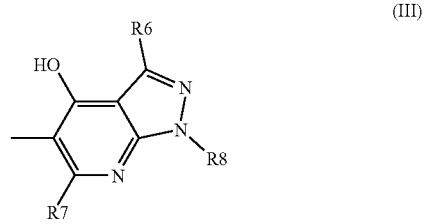

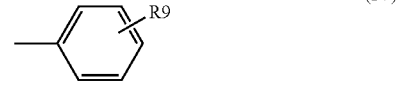

R3 represents a $C_1$-$C_6$-alkyl group, a $C_2$-$C_4$-hydroxy alkyl group or a $C_4$-$C_6$-polyhydroxy alkyl group;

R4 and R5, independent from one another, are either hydrogen, a $C_1$-$C_6$-alkyl amino group, a $C_1$-$C_6$—N,N-dialkyl amino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a benzyl group, or a phenyl group;

R6 and R7, independently from one another, are either hydrogen, an amino group, a $C_1$-$C_6$-alkyl amino group, a $C_1$-$C_6$—N,N-dialkyl amino group, a $C_1$-$C_6$—N,N-(dihydroxy alkyl)amino group, a halogen atom (fluorine, chlorine, bromine or iodine), a cyano group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-hydroxy alkyloxy group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a phenyl group, or a sulfonic acid group;

R8 is either hydrogen, a $C_1$-$C_6$-alkyl amino group, a $C_1$-$C_6$—N,N-dialkyl amino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, or a phenyl group;

R9 is either a hydrogen atom, an amino group, a $C_1$-$C_6$-alkyl amino group, a $C_1$-$C_6$—N,N-dialkyl amino group, a $C_1$-$C_6$-alkyl cyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-alkyl carboxylic acid group, a $C_1$-$C_6$-alkyl carboxylic acid ester group, a $C_1$-$C_6$-alkyl sulfonic acid group, a $C_1$-$C_6$-alkyl sulfonic acid ester group, or a carboxylic acid group (—COOH);

wherein the alkyl groups can either be branched or linear, and $X^-$ represents an anion, preferably a sulfate anion, a phosphate anion, a hydrogen phosphate anion, an oxalate anion, a formate anion, an acetate anion, a citrate anion, a tartrate anion, a malonate anion, a pyruvate anion, an iodide anion, a chloride anion, a bromide anion, or a methylsulfate anion; wherein the chloride anion, bromide anion, and the methylsulfate anion are especially preferred.

The following can be named as suitable cationic direct dyes of the general formula (I):

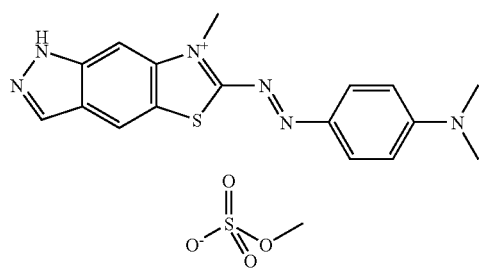

6-{(E)-[4-(dimethylamino)phenyl]diazenyl}-7-methyl-1H-[1,3]thiazolo[5,4-ƒ]indazole-7-ium-methylsulfate, 7-methyl-6-{(E)-[4-(methylamino)phenyl]diazenyl}-1H-[1,3]thiazolo[5,4-ƒ]-indazole-7-ium-methylsulfate,

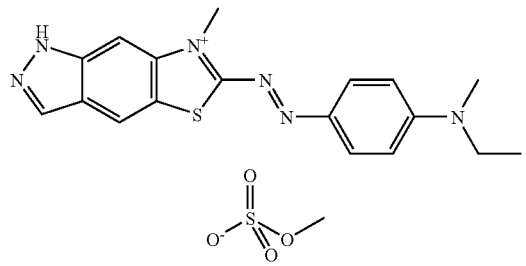

6-{(E)-[4-(ethylamino)phenyl]diazenyl}-7-methyl-1H-[1,3]thiazolo[5,4-ƒ]-indazole-7-ium-methylsulfate,

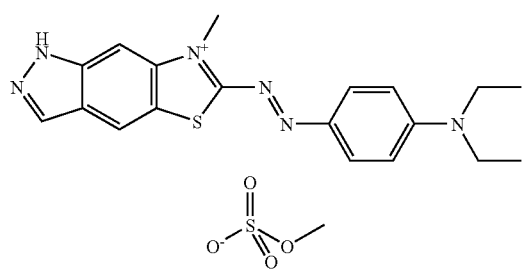

6-{(E)-[4-(diethylamino)phenyl]diazenyl}-7-methyl-1H-[1,3]thiazolo[5,4-ƒ]-indazole-7-ium-methylsulfate,

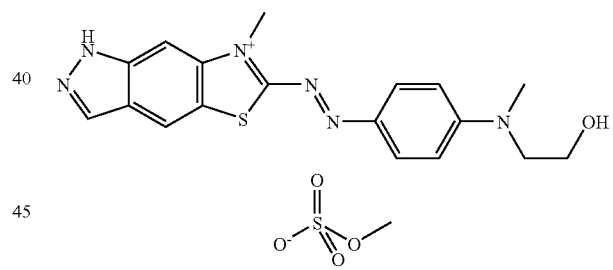

6-((E)-{4-[(2-hydroxyethyl)amino]phenyl}diazenyl)-7-methyl-1H-[1,3]thiazolo[5,4-ƒ]indazole-7-ium-methylsulfate,

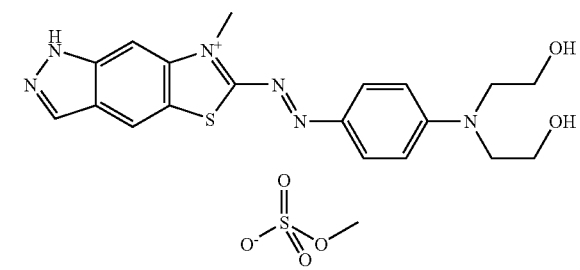

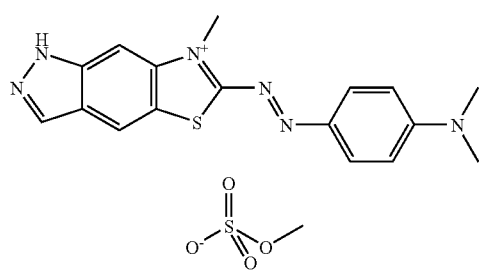

6-((E)-{4-[bis(2-hydroxyethyl)amino]phenyl}diazenyl)-7-methyl-1H-[1,3]thiazolo[5,4-f]indazole-7-ium-methylsulfate, 6-{(E)-[4-(dimethylamino)phenyl]diazenyl}-1,7-dimethyl-1H-[1,3]thiazolo[5,4-ƒ]indazole-7-ium-methylsulfate,

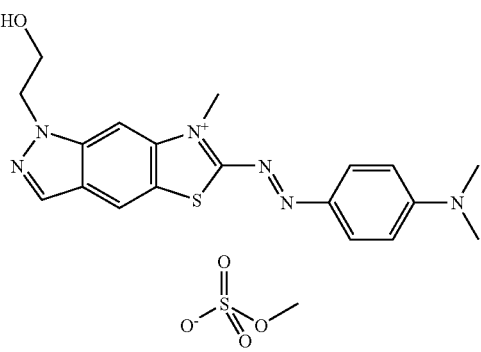

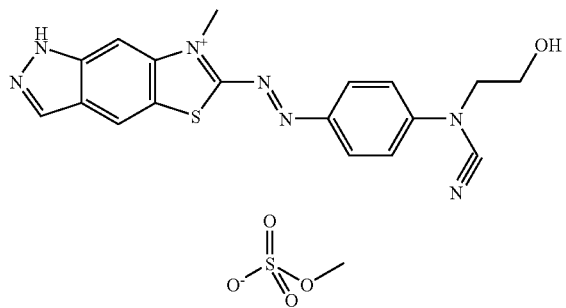

2-hydroxyethyl {4-[(E)-(7-methyl-1H-[1,3]thiazolo[5,4-ƒ]indazole-7-ium-6-yl)diazenyl]phenyl}cyanamid methylsulfate, 6-{(E)-[4-(dimethylamino)phenyl]diazenyl}-1-(2-hydroxyethyl)-7-methyl-1H-[1,3]thiazolo[5,4-f]indazole-7-ium-methylsulfate,

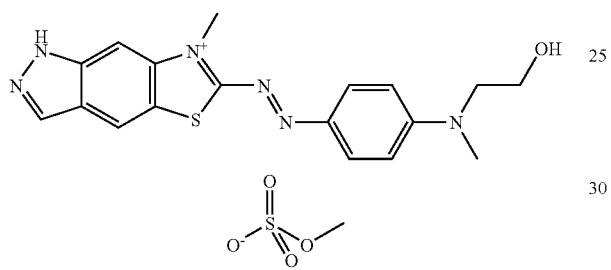

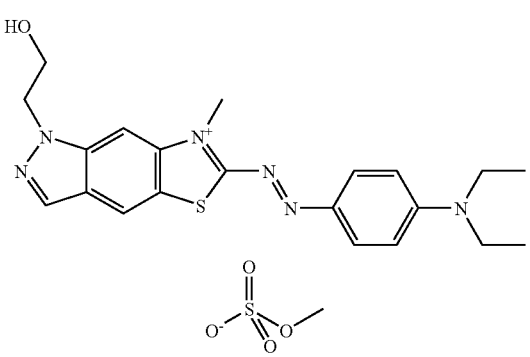

6-((E)-{4-[(2-hydroxyethyl)(methyl)amino]phenyl}diazenyl)-7-methyl-1H-[1,3]thiazolo[5,4-f]indazole-7-ium-methylsulfate,

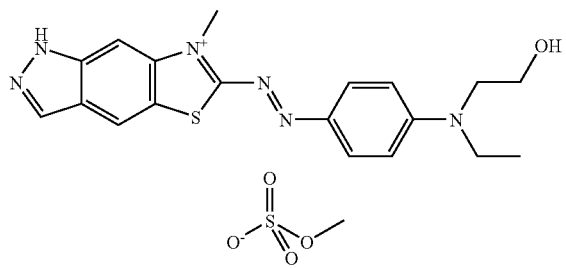

6-({(E)-[4-(diethylamino)phenyl]diazenyl})-1-(2-hydroxyethyl)-7-methyl-1H-[1,3]thiazolo[5,4-f]indazole-7-ium-methylsulfate, 6-((E)-{4-[ethyl(2-hydroxyethyl)amino]phenyl}diazenyl)-7-methyl-1H-[1,3]thiazolo[5,4-f]indazole-7-ium-methylsulfate,

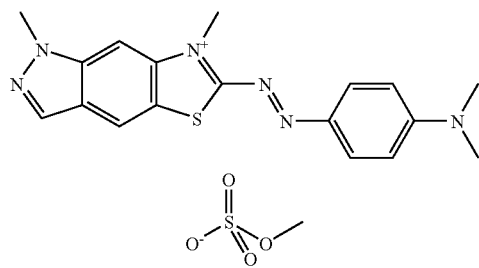

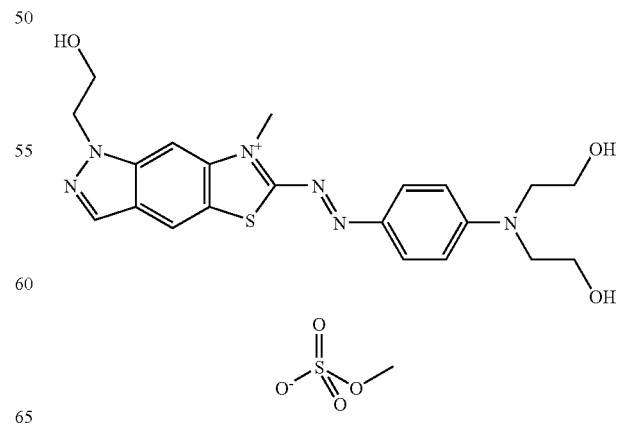

6-((E)-{4-[bis(2-hydroxyethyl)amino]phenyl}diazenyl)-1-(2-hydroxyethyl)-7-methyl-1H-[1,3]thiazolo[5,4-ƒ]indazole-7-ium-methylsulfate,

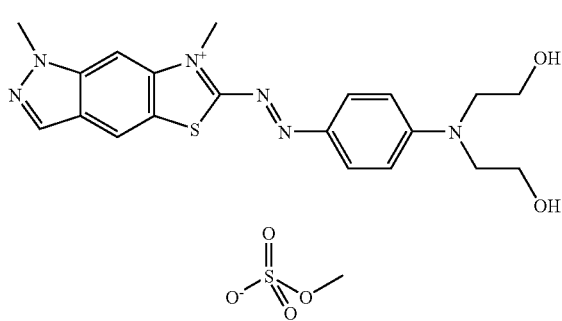

6-((E)-{4-[bis(2-hydroxyethyl)amino]phenyl}diazenyl)-1,7-dimethyl-1H-[1,3]thiazolo[5,4-ƒ]indazole-7-ium-methylsulfate,

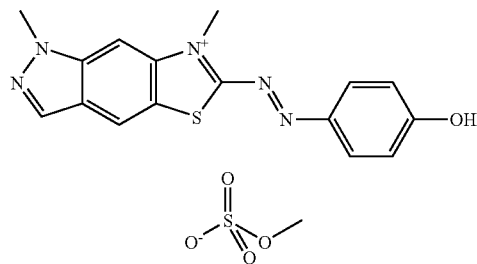

6-[(E)-(4-hydroxyphenyl)diazenyl]-1,7-dimethyl-1H-[1,3]thiazolo[5,4-ƒ]indazole-7-ium-methylsulfate,

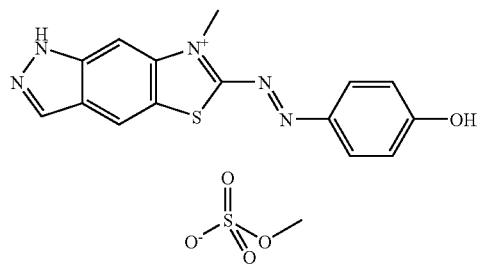

6-[(E)-(4-hydroxyphenyl)diazenyl]-7-methyl-1H-[1,3]thiazolo[5,4-ƒ]indazole-7-ium-methylsulfate,

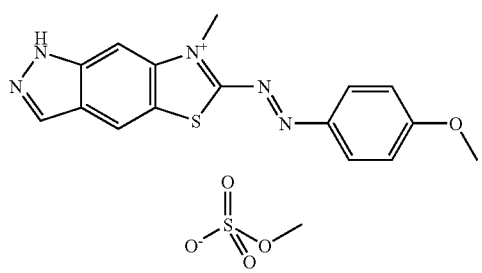

6-[(E)-(4-methoxyphenyl)diazenyl]-7-methyl-1H-[1,3]thiazolo[5,4-ƒ]indazole-7-ium-methylsulfate,

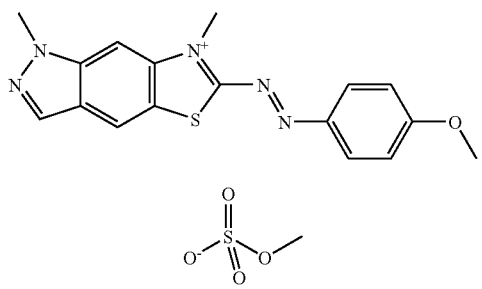

6-[(E)-(4-methoxyphenyl)diazenyl]-1,7-dimethyl-1H-[1,3]thiazolo[5,4-ƒ]indazole-7-ium-methylsulfate,

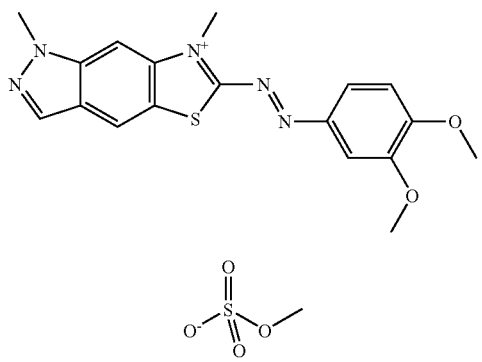

6-[(E)-(3,4-dimethoxyphenyl)diazenyl]-1,7-dimethyl-1H-[1,3]thiazolo[5,4-ƒ]-indazole-7-ium-methylsulfate, and

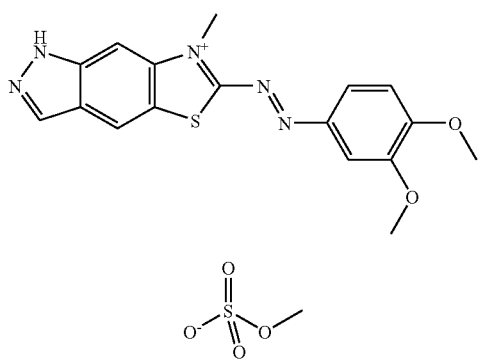

6-[(E)-(3,4-dimethoxyphenyl)diazenyl]-7-methyl-1H-[1,3]thiazolo[5,4-ƒ]indazole-7-ium-methylsulfate.

Especially preferred compounds of the general formula (I) are: 6-{(E)-[4-(dimethylamino)phenyl]diazenyl}-7-methyl-1H-[1,3]thiazolo[5,4-ƒ]indazole-7-ium-methylsulphate, 7-methyl-6-{(E)-[4-(methylamino)phenyl]-diazenyl}-1H-[1,3]thiazolo[5,4-ƒ]indazole-7-ium-methylsulfate, 6-{(E)-[4-(ethyl-amino)phenyl]-iazenyl}-7-methyl-1H-[1,3]thiazolo[5,4-ƒ]indazole-7-ium-methylsulfate, 6-{(E)-[4-(diethylamino)phenyl]diazenyl}-7-methyl-1H-[1,3]thiazolo[5,4-ƒ]-indazole-7-ium-methylsulfate, 6-((E)-{4-[(2-hydroxyethyl)-amino]phenyl}-diazenyl)-7-methyl-1H-[1,3]thiazolo[5,4-ƒ]indazole-7-ium-methylsulfate, 6-((E)-{4-[bis(2-hydroxyethyl)amino]phenyl}diazenyl)-7-methyl-1H-[1, 3]thiazolo[5,4-]indazole-7-ium-methylsulfate, 2-hydroxyethyl {4-[(E)-(7-methyl-1H-[1,3]thiazolo[5,4-f]indazole-7-ium-6-yl)diazenyl]phenyl}cyanamid methylsulfate, 6-((E)-{4-[(2-hydroxyethyl)(methyl)amino]phenyl}diazenyl)-7-methyl-1H-[1,3]thiazolo[5,4-f]indazole-7-ium-methylsulfate, and 6-((E)-{4-[ethyl(2-hydroxyethyl)amino]phenyl}diazenyl)-7-methyl-1H-[1,3]thiazolo[5,4-f]indazole-7-ium-methylsulfate.

The dye derivatives according to the present invention of the general formula (I) are accessible from commercially available or easily producible components via standard operations (Tarabasanu-mihaila, C. et. al., *Revue Roumaine de Chimie*, 1973, 18(5), 889-898).

Thus, the indazoline thiazolazo dyes of the formula (I) can be produced, for example, via a two-stage synthetic process, in which, in a first step, the indazoline thiazolazo compounds of the formula (Ia) can be produced with activated aromates via the azo coupling of 2-aminoindazole thiazoline (e.g., 2-amino-thiazolo[4,5-f]indazole) (FIG. 1); and then, in a second step, the corresponding cationic indazoline thiazolazo dyes of the formula (Ia) can be obtained by converting the compounds of the formula (Ia) with suitable alkylation agents (e.g., DMS=dimethylsulfate) (FIG. 2).

FIG. 1:

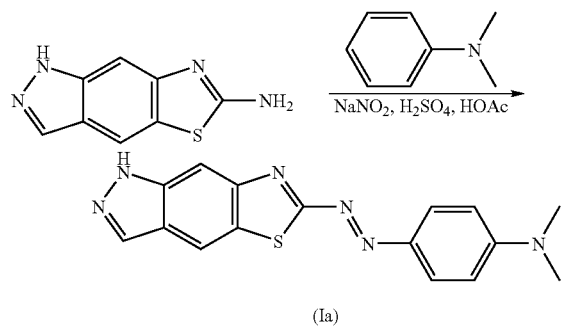

FIG. 2:

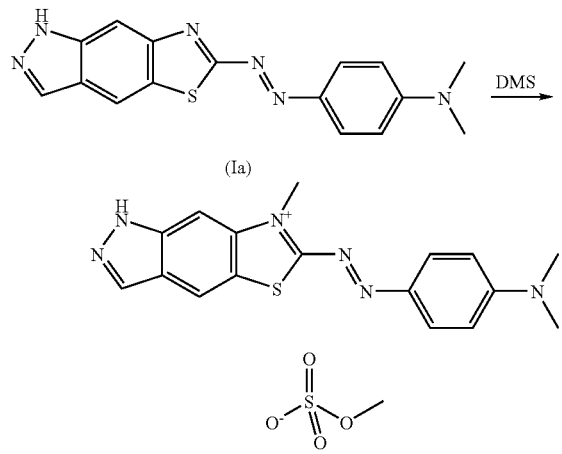

The colorants according to the present invention containing the cationic indazoline thiazolazo dyes of the general formula (I) enable uniform coloring of keratin fibers, particularly human hair, with good stability with respect to light, sweat, and shampooing, wherein intensive, brilliant colors are maintained under gentle conditions.

The cationic indazoline thiazolazo dyes of the general formula (I) are present in the colorants according to the present invention preferably in a total quantity of from 0.01% to 10% by weight, but particularly of from 0.1% to 8% by weight.

The colorant according to the present invention (a) can contain, in addition to the dyes of the general formula (I), other additionally known direct-coloring dyes, either alone or mixed together, from the group consisting of nitro dyes, azo dyes, anthraquinone dyes, and triphenylmethane dyes, such as, for example, 1,4-bis[(2-hydroxyethyl)amino]-2-nitrobenzene, 1-(2-hydroxy-ethyl)amino-2-nitro-4-[di(2-hydroxyethyl)amino]-benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl)amino]-2-nitrobenzene (HC Blue No. 10), 1-[(2,3-dihydroxy-propyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene, (HC Violet No. 2); 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chlorine-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)-benzene, 4-amino-3-nitrophenol, 4-[(2-Hydroxyethyl)amino]-3-nitrophenol, 4-[(2-nitrophenyl)amino]phenol (HC Orange No. 1), 1-[(2-amino-ethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chlorine-4-[(2,3-dihydroxypropyl)amino]-2-nitrobenzene (HC Red No. 10), 5-chlorine-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitro benzoic acid, 2-[(4-amino-2-nitrophenyl)amino]-benzoic acid, 2-chlorine-6-ethylamino-4-nitrophenol, 2-amino-6-chlorine-4-nitrophenol, 4-[(3-hydroxy-propyl)amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazin (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene-hydrochloride, (HC Yellow No. 9), 1-[(2-ureidoethyl)amino]-4-nitrobenzene, 4-[(2,3-dihydroxypropyl)-amino]-3-nitro-1-trifluoromethyl benzene, (HC Yellow No. 6), 1-chlorine-2,4-bis[(2-hydroxyethyl)amino]-5-nitrobenzene (HC Yellow No. 10), 4-[(2-hydroxyethyl)-amino]-3-nitro-1-methyl benzene, 1-chlorine-4-[(2-hydroxyethyl)amino]-3-nitrobenzene (HC Yellow No. 12), 4-[(2-hydroxyethyl)amino]-3-nitro-1-trifluoromethyl benzene, (HC Yellow No. 13), 4-[(2-hydroxyethyl)amino]-3-nitro benzonitrile (HC Yellow No. 14), 4-[(2-hydroxyethyl)amino]-3-nitro benzamide (HC Yellow No. 15), 2,4-dinitro-1-hydroxy naphthalene, 1,4-Di[(2,3-dihydroxy-propyl)amino]-9,10-anthraquinone, 1,4-di[(2-hydroxyethyl)amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)

amino]-9,10-anthraquinone, 7-beta-D-glucopyranosyl-9,10-dihydro-1-methyl-9,10-dioxo-3,5,6,8-tetrahydroxy-2-anthracene carboxylic acid (CI75470, Natural Red 4), 1-[(3-aminopropyl)amino]-9,10-anthraquinone (HC Red No. 8), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chlorine-4-(methylamino)phenyl)imino)-4-methyl-3-oxo-1,4-cyclohexadiene-1-yl)urea (HC Red No. 9), 2-((4-(di(2-hydroxyethyl)amino)phenyl)amino)-5-((2-hydroxyethyl)amino)-2,5-cyclohexadiene-1,4-dion (HC Green No. 1), 2-hydroxy-1,4-naphthoquinone (CI75480, Natural Orange No. 6), 1,2-dihydro-2-(1,3-dihydro-3-oxo-2H-indole-2-ylidene)-3H-indole-3-on (CI73000), 1,3-bis(dicyanomethylene)indane, di[4-(diethylamino)phenyl][4-(ethylamino)naphthyl]carbenium chloride (CI42595; Basic Blue No. 7), di[4-(dimethylamino)phenyl][4-(phenylamino)naphthyl]-carbenium chloride (CI44045; Basic Blue No. 26), Basic Blue No. 77, 8-amino-2-bromine-5-hydroxy-4-imino-6-[(3-(trimethylammonio)phenyl)amino]-1(4H)-naphthalenone chloride (CI56059; Basic Blue No. 99), tri(4-amino-3-methylphenyl)carbenium chloride (CI42520; Basic Violet No. 2), di(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)-azo]-N,N,N-trimethylbenzene aminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium-chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium-chloride (Basic Red No. 51), 2-hydroxy-1-[(2-methoxyphenyl)azo]-7-(trimethylammonio)naphthalene chloride (CI12245; Basic Red No. 76), 3-methyl-1-phenyl-4-[(3-(trimethylammonio)phenyl)azo]-pyrazol-5-on-chloride (CI12719; Basic Yellow No. 57), 1-methyl-4-((methylphenyl-hydrazono)methyl)pyridinium methylsulfate (Basic Yellow No. 87), 1-(2-morpholinium propylamino)-4-hydroxy-9,10-anthraquinone methylsulfate, 1-[(3-(dimethylpropylaminium)propyl)amino]-4-(methylamino)-9,10-anthraquinone chloride, 1-[Di(2-hydroxyethyl)amino]-3-methyl-4-[(4-nitrophenyl)-azo]benzene (CI11210, Disperse Red No. 17), 1-[di(2-hydroxyethyl)amino]-4-[(4-nitrophenyl)azo]benzene, (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]pyridine, and 2-((4-(ethyl(2-hydroxyethyl)-amino)-2-methylphenyl)azo)-5-nitro-1,3-thiazole (CI 11935; Disperse Blue No. 106).

The colorant (b) according to the present invention, which distinguishes itself by contents comprising an oxidizing agent, preferably hydrogen peroxide, and/or persulfates, which are preferably perborates and, in particular, persulfates, or a mixture of hydrogen peroxide and persulfates, can also contain, in addition to the dyes of the general formula, other oxidation-stable, direct-coloring dyes, such as, for example, 3-(2',6'-diaminopyridyl-3'-azo)pyridine (=2,6-diamino-3-((pyridin-3-yl)azo)pyridine, 2-((4-(ethyl(2-hydroxyethyl)-amino)-2-methylphenyl)azo-5-nitro-1,3-thiazole (Disperse Blue 106), N,N-di(2-hydroxyethyl)-3-methyl-4-((4-nitrophenyl)azo)aniline (Disperse Red 17, CI 11210), 3-diethylamino-7-(4-dimethylaminophenylazo)-5-phenylphenazinium chloride (CI11050), 4-(2-thiazolylazo)resorcinol, 4-(((4-phenylamino)azo)benzosulfonic acid sodium salt (Orange IV), 1-((3-aminopropyl)amino)-9,10-anthracenedione (HC Red No. 8), 3',3",4,5,5',5",6,7-octabromo phenol sulfonphthalein (Tetrabromphenol Blue), 1-((4-amino-3,5-dimethylphenyl)-(2,6-dichlorophenyl)-methylene)-3,5-dimethyl-4-imino-2,5-cyclohexadiene phosphoric acid (1:1) (Basic Blue 77), 3',3",5',5"-tetrabromo-m-cresolsulfonphthalein, 2,4-dinitro-1-naphthol-7-sulfonic acid disodium salt (Acid Yellow 1, CI 10316), 4-[2'-hydroxy-1'-naphthyl)azo]benzosulfonic acid-sodium salt (Acid Orange 7, CI 15510), 3',6'-dihydroxy-2',4',5',7'-tetraiodospiro-[isobenzo-furan-1 (3H), 9'(9H)-xanthene]-3-on-disodium salt (Acid Red 51, CI45430), 6-hydroxy-5-((2-methoxy-5-methyl-4-sulfophenyl)azo)-2-naphthalene sulfonic acid disodium salt (FD&C Red 40, CI16035), 2,4-dinitro-1-naphthol-sodium salt (Acid Yellow 24; CI10315), 2',4',5',7'-tetrabromo-4,5,6,7-tetrachloro-3',6'-dihydroxy-spiro(isobenzofuran-1(3H), 9'[9H] xanthene]-3-on-disodium salt (Acid Red 92; CI45410), 4-(2-hydroxy-1-naphthylazo)-3-methylbenzene sulfonic acid sodium salt (Acid Orange 8, CI 15575), 2-amino-1,4-naphthalenedione, dithizone (1,5-diphenylthiocarbazone), N-(2-hydroxyethyl))-2-nitro-4-trifluoromethyl)aniline (HC Yellow 13), N-(2-hydroxyethyl)-4-nitro-aniline, and 4-chlorine-N-(2,3-dihydroxypropyl)-2-nitro-aniline.

The aforementioned direct-penetrating dyes can be present in a total quantity of 0.01% to 4% by weight, wherein the total content of dyes in the colorant according to the present invention is preferably 0.01% to 10% percent by weight, but particularly 0.1% to 5% by weight.

The oxidation colorant (c) according to the present invention, which is mixed with an oxidizing agent (particularly hydrogen peroxide or addition compounds thereof)—alternatively, the oxidation can also occur via atmospheric oxygen, with the use of suitable enzymes as needed—contains additional oxidative dye precursors, in addition to the dyes of the general formula (I).

The following developer substances and coupler substances as well as compounds coupling with themselves, for example, can be named as suitable oxidative dye precursors:

(i) Developer substances: 1,4-diamino benzene (p-phenylendiamine), 1,4-diamino-2-methylbenzene (p-toluoylenediamine), 1,4-diamino-2,6-xylene, 1,4-diamino-3,5-diethylbenzene, 1,4-diamino-2,5-xylene, 1,4-diamino-2,3-xylene, 2-chlorine-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diamino biphenyl, 1,4-diamino-2-methoxymethyl benzene, 1,4-diamino-2-aminomethyl benzene, 1,4-diamino-2-hydroxymethyl benzene, 1,4-diamino-2-(2-hydroxyethoxy)benzene, 2-(2-(acetylamino)ethoxy)-1,4-diamino benzene, 4-phenylamino aniline, 4-dimethylamino aniline, 4-diethylamino aniline, 4-dipropylamino aniline, 4-[ethyl(2-hydroxyethyl)-amino]aniline, 4-[di(2-hydroxyethyl)amino]aniline, 4-[di(2-hydroxyethyl)amino]-2-methyl aniline, 4-[(2-methoxyethyl) amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl) benzene, 1,3-bis[(4-aminophenyl)(2-hydroxyethyl)amino]-2-propanol, 1,4-bis[(4-aminophenyl)amino]butane, 1,8-bis (2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxy-ethyl)-amino]methylphenol, 4-amino-2-methylphenol, 4-amino-2-(methoxymethyl)phenol, 4-amino-2-(2-hydroxyethyl)phenol, 5-amino salicylic acid, 2,5-diamino pyridine, 2,4,5,6-tetramino pyrimidine, 2,5,6-triamino-4-(1H)-pyrimidone, 4,5-diamino-1-(2-hydroxyethyl)-1H-pyrazol, 4,5-diamino-1-(1-methylethyl)-1H-pyrazol, 4,5-diamino-1-[(4-methylphenyl)-methyl]-1H-pyrazol, 1-[(4- chlorophenyl)methyl]-4,5-diamino-1H-pyrazol, 4,5-diamino-1-methyl-1H-pyrazol, 2-aminophenol, 2-amino-6-methylphenol, 2-amino-5-methylphenol, alone or mixed with each other.

(ii) Coupler substances: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxy-ethoxy)-5-methylbenzene, 2,4-di[(2-hydroxyethyl)amino]-1,5-dimethoxybenzene, 2,3-diamino-6-methoxy pyridine, 3-amino-6-methoxy-2-(methylamino)pyridine, 2,6-diamino-3,5-dimethoxy pyridine, 3,5-diamino-2,6-dimethoxy pyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxy acetic acid, 3-[di(2-hydroxy-ethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy)propane, Di(2,4-diamino phenoxy)methane, 1,3-diamino-2,4-dimethoxybenzene, 2,6-bis(2-hydroxy-ethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chlorine-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)-amino]-2-methylphenol, 2-amino-3-hydroxypyridine, 5-amino-4-chlorine-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chlorine-2,4-dihydroxybenzene, 2-chlorine-1,3-dihydroxybenzene, 1,2-dichloro-3,5-dihydroxy-4-methylbenzene, 1,5-dichloro-2,4-dihydroxybenzene, 1,3-dihydroxy -2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diamino benzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indoline dione, alone or mixed with each other.

(iii) Compounds coupling with themselves: 2-amino-5-methylphenol, 2-amino-6-methylphenol, 2-amino-5-ethoxyphenol, or 2-propylamino-5-aminopyridine.

The total quantity of the oxidative dye precursors contained in the colorant (c) according to the present invention is 0.01% to 12% by weight, but particularly 0.2% to 6% by weight.

The colorant (a), (b), or (c) according to the present invention can also contain all customary additives known for these types of preparations, for example, perfume oils, chelating agents, waxes, preservatives, thickeners, antioxidants, alginates, guar gum, hair-conditioning substances, such as, for example, cationic polymers, or lanolin derivatives, or anionic, nonionic, amphoteric, or cationic, surface-active substances. The following are preferably used: amphoteric or nonionic surface-active substances, for example, betaine surfactants, propoinates, and glycinates, such as, for example, cocoampho glycinates or cocoampho diglycinates, ethoxylated surfactants with 1 to 1000 ethylene oxide units, preferably with 1 to 300 ethylene oxide units, such as, for example, glyceride alkoxylates, for example, with 25 ethylene oxide units of an ethoxylated castor oil, polyglycolamides, ethoxylated alcohols, and ethoxylated fatty alcohols (fatty alcohol oxylates), as well as ethoxylated fatty acid sugar esters, in particular, ethoxylated sorbitan fatty acid esters. The aforementioned components are used in the quantities customary for such purposes, for example, the surface-active substances in a concentration of from 0.1% to 30% by weight and the conditioning agents in a quantity of from 0.1% to 5% by weight.

The colorant (a), (b), or (c) according to the present invention, particularly if it is a hair colorant, can be present in the form of a powder or granulate, which is dissolved in an aqueous or aqueous-alcohol preparation before application, or, however, an aqueous or aqueous-alcohol solution, a cream, a gel, an emulsion, or an aerosol foam, wherein the hair colorant can be mass-produced both in the form of a single-component preparation or in the form of a multi-component preparation, for example, with which the particular dye derivative of the general formulas (I) and (II) are packaged separately from the other components, and the ready-to-use hair colorant is not produced until immediately before its use via a mixing of both components.

The colorant (a), (b), or (c) according to the present invention normally has a pH of 2 to 11, with about 5 to 10 being preferred, and, in particular, a neutral to basic pH value of 7 to 10. Either organic or inorganic acids or bases can be used to achieve the pH value according to the present invention. In particular, the following acids can be named as suitable acids: α-hydroxy carboxylic acids, such as glycolic acid, lactic acid, tartaric acid, citric acid, or malic acid, ascorbic acid, gluconic acid lactone, acetic acid, hydrochloric acid, or phosphoric acid, as well as mixtures of these acids. The following can be named, in particular, as suitable bases: sodium carbonate, sodium bicarbonate, alkanolamines, for example, monoethanolamine or triethanolamine, ammonia, aminomethylpropanol, and sodium hydroxide, as well as mixtures thereof.

The colorant according to the present invention can, depending on the particular targeted application, be used with one or more oxidizing agents (lightening, oxidation colorant) or without an oxidizing agent (non-oxidative colorant).

The colorant according to the present invention is normally used by applying a quantity of the colorant that is sufficient for coloring the hair, which is 30 grams to 120 grams depending on hair length, to the hair, allowing the hair colorant to act on the hair at 15° C. to 45° C. for 1 minute to 60 minutes, preferably 5 minutes to 30 minutes, thoroughly rinsing the hair with water, and, if necessary, washing it with shampoo and/or treating with a hair conditioner, and subsequently drying.

If necessary, the agent is mixed with an oxidizing agent before application.

The previously described colorant can also contain, as long as no oxidizing agent of the color mixture is to be added, natural or synthetic polymers that are customary for cosmetic agents or modified polymers of natural origin, whereby the hair is strengthened at the same time it is colored. Such agents are generally characterized as tinting strengtheners or color strengtheners.

The following can be mentioned from the synthetic polymers known in the cosmetic industry for this purpose: polyvinylpyrrolidone, polyvinylacetate, polyvinylalcohol, or polyacryl compounds such as polyacrylic acid or polymethacrylic acid, basic polymerisates of esters of polyacrylic acid, polymethylacrylic acid, and alkanolamines, for example, salts thereof or quaternization products, polyacrylic nitrile, polyvinylacetates, as well as copolymerisates from these types of compounds, such as, for example, polyvinylpyrrolidone vinylacetate; whereas, for example, chitosan (de-acetylized chitin) or chitosan derivatives can be used as natural polymers or modified natural polymers.

The aforementioned polymers can be present in the colorant (a) according to the present invention in the quantities customary for such agents, in particular, in a quantity of 1% to 5% by weight. The pH value of the tinting strengthener or color strengthener according to the present invention is preferably about 6 to 9.

The hair colorant with the additional strengthening is applied in the known and customary manner by dampening the hair with the strengthener, setting the hair in the desired style, and then drying.

The colorants (a), (b) and (c) enable uniform, intensive, and permanent coloring of keratin fibers (for example, human hair, wool, or fur) without any significant coloring of the skin or scalp, wherein this coloring lasts, in the case of colorant (a) for five or more hair washings without any noticeable fading in the hair color.

The following examples are intended to provide further explanation of the object of the present invention without limiting the invention to these examples.

EXAMPLES

Example 1

Hair Colorant without Oxidizing Agent

| 2.5 mmol | dye of the general formula (I) |
| --- | --- |
| 5.0 g | ethanol |
| 4.0 g | decyl polyglucose |
| 0.2 g | ethylenediaminotetraacetic acid disodium salt hydrate |
| balance to 100.0 g | water, completely desalinated |

The color solution is adjusted to a pH value of 7 to 10 by the addition of ammonia.

The hair is colored by applying a quantity of colorant to the hair that is sufficient for coloring the hair. After an application time of 30 minutes at 40° C., the hair is rinsed with lukewarm water and dried.

The coloring results are compiled in Table 1.

TABLE 1

| Dye of the general formula (I) | Coloring |
| --- | --- |
| 6-{(E)-[4-(dimethylamino)phenyl]diazenyl}-7-methyl-1H-[1,3]thiazolo[5,4-f]indazole-7-ium-methylsulfate | Blue |
| 6-{(E)-[4-(diethylamino)phenyl]diazenyl}-7-methyl-1H-[1,3]thiazolo[5,4-f]indazole-7-ium-methylsulfate | Royal blue |

Example 2

Hair Colorant for Simultaneous Lightening and Coloring (with Oxidizing Agent)

| Lightening powder basis P: | |
| --- | --- |
| 20.0 g | potassium persulfate |
| 30.0 g | ammonium persulfate |
| 24.0 g | sodium silicate |
| 12.5 g | magnesium oxide |
| 5.0 g | hydroxyethylcellulose |
| 6.0 g | soap beads |
| 2.0 g | dispersed hydrated silica |
| 0.5 g | disodium ethylenediaminetetraacetate |

| Ready-to-use hair colorant: | |
| --- | --- |
| 0.1 g | dye of the general formula (I) |
| 5.0 g | lightening powder basis P |
| 10.0 g | hydrogen peroxide (12% in water) |

The components indicated are mixed to form a homogenous mass until no more dye particles can be seen. At that point, a quantity of the aforementioned color mixture sufficient to color the hair is applied to the hair. After an application time of 45 minutes at 40° C., the hair is rinsed with lukewarm water and treated with an acidic conditioner, then rinsed again and dried.

The coloring results are compiled in Table 2.

TABLE 2

| Dye of the general formula (I) | Coloring |
| --- | --- |
| 6-{(E)-[4-(dimethylamino)phenyl]diazenyl}-7-methyl-1H-[1,3]thiazolo[5,4-f]indazole-7-ium-methylsulfate | Blue |
| 6-{(E)-[4-(diethylamino)phenyl]diazenyl}-7-methyl-1H-[1,3]thiazolo[5,4-f]indazole-7-ium-methylsulfate | Dark blue |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for non-oxidative coloring of keratin fibers, comprising at least one cationic indazoline thiazolazo dye of the general formula (I),
wherein

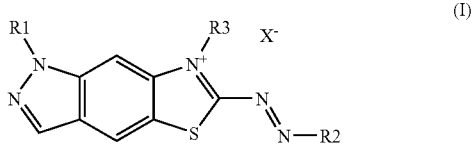

R1 stands for a hydrogen atom, a $C_1$-$C_6$-alkyl amino group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, and a $C_1$-$C_6$-alkyl sulfonic acid ester group;

R2 represents a group of the general formulas (II), (III), or (IV);

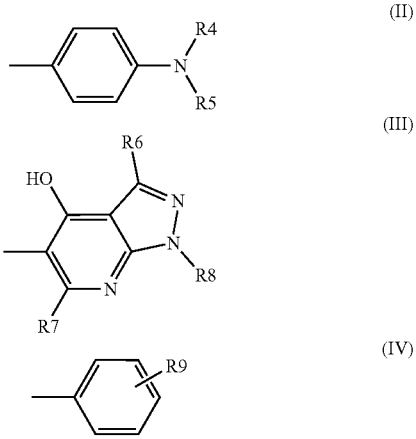

R3 represents a $C_1$-$C_6$-alkyl group, a $C_2$-$C_4$-hydroxy alkyl group or a $C_4$-$C_6$-polyhydroxy alkyl group;

R4 and R5, independently from one another, are either hydrogen, a $C_1$-$C_6$-alkyl amino group, a $C_1$-$C_6$-N-N-dialkyl amino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a benzyl group, or a phenyl group;

R6 and R7, independently from one another, are either hydrogen, an amino group, a $C_1$-$C_6$-alkylamino group, a $C_1$-$C_6$-N,N-dialkylamino group, a $C_1$-$C_6$-N,N-(dihydroxyalkyl)amino group, a halogen atom, a cyano group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxy alkyloxy group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a phenyl group, or a sulfonic acid group;

R8 is either hydrogen, a $C_1$-$C_6$-alkylamino group, a $C_1$-$C_6$—N,N-dialkyl amino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, or a phenyl group;

R9 is either a hydrogen atom, an amino group, a $C_1$-$C_6$-alkyl amino group, a $C_1$-$C_6$—N,N-dialkyl amino group, a $C_1$-$C_6$-alkyl cyano group, a hydroxyl group, a nitro group, a methoxymethyl group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, a $C_1$-$C_6$-alkyl sulfonic acid ester group, or a carboxylic acid group (—COOH);

wherein the alkyl groups can either be branched or linear, and $X^-$ represents an anion;

wherein said agent comprises at least one natural polymer, synthetic polymer, or modified polymer of natural origin customary for cosmetic agents, wherein said natural polymer, synthetic polymer, or modified polymer is present in the form of a tinting strengthener or a color strengthener.

2. An agent according to claim 1, wherein the cationic indazoline thiazolazo dye of the general formula (I) is selected from the group consisting of 6-{(E)-[4-(dimethylamino)phenyl]diazenyl}-7-methyl-1H-[1,3]thiazolo[5,4-f]indazole-7-ium-methylsulfate, 7-methyl-6-{(E)-[4-(methylamino)phenyl]diazenyl}-1H-[1,3]thiazolo[5,4-f]indazole-7-ium-methylsulfate, 6-{(E)-[4-(ethylamino)phenyl]diazenyl}-7-methyl-1H-[1,3]thiazolo[5,4-f]indazole-7-ium-methylsulfate, 6-{(E)-[4-(diethylamino)-phenyl]diazenyl}-7-methyl-1H-[1,3]thiazolo[5,4-f]indazole-7-ium-methylsulfate, 6-((E)-{4-[(2-hydroxyethyl)amino]phenyl}diazenyl)-7-methyl-1H-[1,3]thiazolo-[5,4-f]indazole-7-ium-methylsulfate, 6-((E)-{4-[bis(2-hydroxyethyl)amino]phenyl}-diazenyl)-7-methyl-1H-[1,3]thiazolo[5,4-f]indazole-7-ium-methylsulfate, 2-hydroxyethyl {4-[(E)-(7-methyl-1H-[1,3]thiazolo[5,4-f]indazole-7-ium-6-yl)diazenyl]phenyl}cyanamid methylsulfate, 6-((E)-{4-[(2-hydroxyethyl)(methyl)-amino]phenyl}diazenyl)-7-methyl-1H-[1,3]thiazolo[5,4-f]indazole-7-ium-methylsulfate, 6-((E)-{4-[ethyl(2-hydroxyethyl)amino]phenyl}diazenyl)-7-methyl-1H-[1,3]thiazolo[5,4-f]indazole-7-ium-methylsulfate, 6-{(E)-[4-(dimethylamino)-phenyl]diazenyl}-1,7-dimethyl-1H-[1,3]thiazolo[5,4-f]indazole-7-ium-methylsulfate, 6-{(E)-[4-(dimethylamino)phenyl]diazenyl}-1-(2-hydroxyethyl)-7-methyl-1H-[1,3]thiazolo[5,4-f]indazole-7-ium-methylsulfate, 6-{(E)-[4-(diethylamino)-phenyl]diazenyl}-1-(2-hydroxyethyl)-7-methyl-1H-[1,3]thiazolo[5,4-f]indazole-7-ium-methylsulfate, 6-((E)-{4-[bis(2-hydroxyethyl)amino]phenyl}diazenyl)-1-(2-hydroxyethyl)-7-methyl-1H-[1,3]thiazolo[5,4-f]indazole-7-ium-methylsulfate, 6-((E)-{4-[bis(2-hydroxyethyl)amino]phenyl}diazenyl)-1,7-dimethyl-1H-[1,3]thiazolo[5,4-f]indazole-7-ium-methylsulfate, 6-[(E)-(4-hydroxyphenyl)diazenyl]-1,7-dimethyl-1H-[1,3]thiazolo[5,4-f]indazole-7-ium-methylsulfate, 6-[(E)-(4-hydroxyphenyl)diazenyl]-7-methyl-1H-[1,3]thiazolo[5,4-f] indazole-7-iummethylsulfate, 6-[(E)-(4-methoxyphenyl)diazenyl]-7-methyl-1H-[1,3]thiazolo[5,4-f]indazole-7-ium-methylsulfate, 6-[(E)-(4-methoxyphenyl)-diazenyl]-1,7-dimethyl-1H-[1,3]thiazolo[5,4-f]indazole-7-ium-methylsulfate, 6-[(E)-(3,4-dimethoxyphenyl)diazenyl]-1,7-dimethyl-1H-[1,3]thiazolo[5,4-f]indazole-7-ium-methylsulfate, and 6-[(E)-(3,4-dimethoxyphenyl)diazenyl]-7-methyl-1H-[1,3]thiazolo[5,4-f]indazole-7-ium-methylsulfate.

3. An agent according to claim 1, wherein the cationic indazoline thiazolazo dye of the general formula (I) is present in a total quantity of 0.01% to 10% by weight of said agent.

4. An agent according to claim 1, wherein it is a hair colorant.

5. An agent for simultaneous lightening and coloring of keratin fibers, comprising,
(i) on oxidizing agent; and
(ii) at least one cationic indazoline thiazolazo dye of the general formula (I);

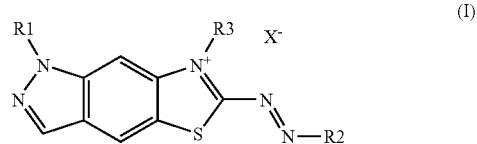

wherein
R1 is selected from the group consisting of a hydrogen atom, a $C_1$-$C_6$-alkyl amino group, a tert-butyl group, a isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, and a $C_1$-$C_6$-alkyl sulfonic acid ester group;
R2 is selected from the group consisting of the general formulas (II), (III), and (IV);

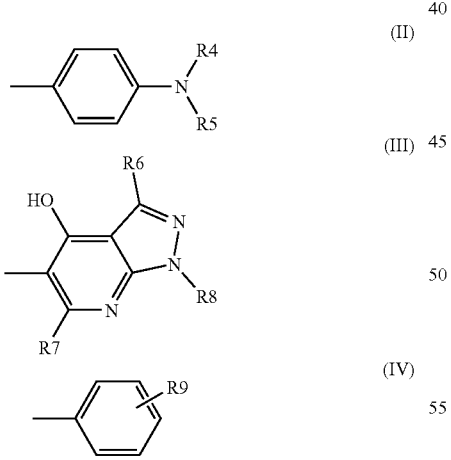

R3 is selected from the group consisting of a $C_1$-$C_6$-alkyl group, a $C_2$-$C_4$-hydroxy alkyl group and a $C_4$-$C_6$-polyhydroxy alkyl group;
R4 and R5, independently from one another, are selected from the group consisting of a
$C_1$-$C_6$-alkylamino group, a $C_1$-$C_6$—N,N-dialkylamino group, a
$C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a benzyl group, and a phenyl group;
R6 and R7, independently from one another, are selected from the group consisting of hydrogen, an amino group, a $C_1$-$C_6$-alkylamino group, a $C_1$-$C_6$—N,N-dialkylamino group, a $C_1$-$C_6$—N,N-(dihydroxyalkyl)amino group, a halogen atom, a cyano group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl acid group, a $C_1$-$C_6$-hydroxy alkyloxy group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a phenyl group, and a sulfonic acid group;
R8 is selected from the group consisting of hydrogen, a $C_1$-$C_6$-alkyl amino group, a $C_1$-$C_6$—N,N-dialkylamino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, and a phenyl group;
R9 is selected from the group consisting of a hydrogen atom, an amino group, a $C_1$-$C_6$-alkyl amino group, a $C_1$-$C_6$—N,N-dialkyl amino group, a $C_1$-$C_6$-alkyl cyano group, a hydroxyl group, a nitro group, a methoxymethyl group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, a $C_1$-$C_6$-alkyl sulfonic acid ester group, and a carboxylic acid group (—COOH);
wherein the alkyl groups can either be branched or linear, and
$X^-$ represents an anion.

6. An agent according to claim 5, wherein the oxidizing agent is selected from the group consisting of hydrogen peroxide, persulfates, perborates, and mixtures of these compounds.

7. An agent for oxidative coloring of keratin fibers based on oxidative dye precursors, comprising at least one cationic indazoline thiazolazo dye of the general formula (I),

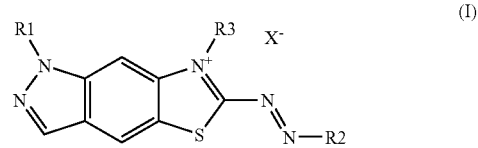

wherein
R1 is selected from the group consisting of a hydrogen atom, a $C_1$-$C_6$-alkyl amino group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, and a $C_1$-$C_6$-alkyl sulfonic acid ester group;

R2 is selected from the group consisting of a the general formulas (II), (III), and (IV);

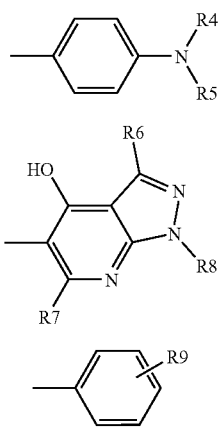

R3 is selected from the group consisting of a $C_1$-$C_6$-alkyl group, a $C_2$-$C_4$-hydroxy alkyl group and a $C_4$-$C_6$-polyhydroxy alkyl group;

R4 and R5, independently from one another, are selected from the group consisting of hydrogen, a $C_1$-$C_6$-alkyl amino group, a $C_1$-$C_6$—N,N-dialkyl amino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxy alkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a benzyl group, and a phenyl group;

R6 and R7, independently from one another, are selected from the group consisting of hydrogen, an amino group, a $C_1$-$C_6$-alkylamino group, a $C_1$-$C_6$—N,N-dialkylamino group, a $C_1$-$C_6$—N,N-(dihydroxyalkyl)amino group, a halogen atom, a cyano group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxy alkyloxy group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, a phenyl group, and a sulfonic acid group;

R8 is selected from the group consisting of hydrogen, a $C_1$-$C_6$-alkylamino group, a $C_1$-$C_6$—N,N-dialkylamino group, a $C_1$-$C_6$-alkyl cyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl carboxylic acid amide group, a $C_1$-$C_6$-alkyl sulfonic acid group, a $C_1$-$C_6$-alkyl sulfonic acid ester group, a $C_1$-$C_6$-alkyl sulfonic acid amide group, and a phenyl group;

R9 is selected from the group consisting of a hydrogen atom, an amino group, a $C_1$-$C_6$-alkylamino group, a $C_1$-$C_6$—N,N-dialkylamino group, a $C_1$-$C_6$-alkyl cyano group, a hydroxyl group, a nitro group, a methoxymethyl group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkyl carboxylic acid group, a $C_1$-$C_6$-alkyl carboxylic acid ester group, a $C_1$-$C_6$-alkyl sulfonic acid group, a $C_1$-$C_6$-alkyl sulfonic acid ester group, and a carboxylic acid group (—COOH);

wherein the alkyl groups can either be branched or linear, and $X^-$ represents an anion.

8. An agent according to claim 7, comprising 0.01% to 12% by weight of at least one oxidative dye precursor.

9. An agent according to claim 7, wherein said agent is mixed with an oxidizing agent before use.

* * * * *